(12) United States Patent
Johannesson et al.

(10) Patent No.: US 8,213,025 B2
(45) Date of Patent: Jul. 3, 2012

(54) METHOD AND APPARATUS FOR DETERMINING THE AMOUNT OF SCATTERED LIGHT IN A MACHINE VISION SYSTEM

(75) Inventors: Mattias Johannesson, Linkoping (SE); Henrik Turbell, Linkoping (SE); Per Holm, Linkoping (SE)

(73) Assignee: Sick IVP AB, Linkoping (SE)

( * ) Notice: Subject to any disclaimer, the term of this patent is extended or adjusted under 35 U.S.C. 154(b) by 247 days.

(21) Appl. No.: 12/531,421

(22) PCT Filed: Apr. 25, 2008

(86) PCT No.: PCT/SE2008/050473
§ 371 (c)(1),
(2), (4) Date: Jan. 28, 2010

(87) PCT Pub. No.: WO2008/133588
PCT Pub. Date: Nov. 6, 2008

(65) Prior Publication Data
US 2010/0141946 A1    Jun. 10, 2010

(30) Foreign Application Priority Data
Apr. 26, 2007    (EP) .................................. 07107045

(51) Int. Cl.
*G01B 11/14* (2006.01)
(52) U.S. Cl. .................. 356/625; 356/630; 356/601
(58) Field of Classification Search .......... 356/601–625, 356/4.01, 4.07, 5.09, 628, 630; 250/205, 250/206.1, 559.38
See application file for complete search history.

(56) References Cited

U.S. PATENT DOCUMENTS

| | | | |
|---|---|---|---|
| 4,334,780 A | 6/1982 | Pernick | |
| 4,741,621 A * | 5/1988 | Taft et al. | 356/606 |
| 5,608,527 A * | 3/1997 | Valliant et al. | 356/600 |
| 5,668,631 A * | 9/1997 | Norita et al. | 356/608 |
| 6,369,401 B1 * | 4/2002 | Lee | 250/559.21 |
| 6,542,249 B1 * | 4/2003 | Kofman et al. | 356/601 |
| 6,819,407 B2 * | 11/2004 | Arita et al. | 356/4.01 |

(Continued)

FOREIGN PATENT DOCUMENTS

EP    1 612 509    1/2006

(Continued)

OTHER PUBLICATIONS

Extended European Search Report for Application No. 07107045.2, dated Oct. 11, 2001, 8 pages.
Authorized Officer Anna Lundqvist, International Search Report for Application No. PCT/SE2008/050473, dated Jul. 21, 2008.

*Primary Examiner* — Sang Nguyen
(74) *Attorney, Agent, or Firm* — Fish & Richardson P.C.

(57) ABSTRACT

The present invention relates to a method and an apparatus for determining the amount of light scattered in an object in a machine vision system comprising: a light source illuminating said object with incident light having a limited extension in at least one direction; and, an imaging sensor detecting light emanating from said object, wherein said emanated light is reflected light (R) on the surface of said object and light scattered (S) in said object, said detected light is resulting in at least one intensity distribution curve on said imaging sensor having a peak where said reflected light (R) is detected on said imaging sensor. A width (w) of said at least one intensity distribution curve around said peak is measured, whereby said measured width (w) indicates the amount of light scattered (S) in said object.

17 Claims, 4 Drawing Sheets

U.S. PATENT DOCUMENTS

| | | | |
|---|---|---|---|
| 7,084,989 B2 * | 8/2006 | Johannesson et al. | 356/601 |
| 7,502,102 B2 * | 3/2009 | Johannesson et al. | 356/237.2 |
| 7,633,511 B2 * | 12/2009 | Shum et al. | 345/628 |
| 7,645,974 B2 * | 1/2010 | Ikeno et al. | 250/205 |
| 2004/0234118 A1 * | 11/2004 | Astrom et al. | 382/141 |
| 2008/0055591 A1 * | 3/2008 | Walton | 356/237.1 |
| 2008/0123106 A1 * | 5/2008 | Zeng et al. | 356/600 |
| 2008/0204763 A1 * | 8/2008 | Turbell et al. | 356/601 |

FOREIGN PATENT DOCUMENTS

| | | |
|---|---|---|
| WO | WO 95/24636 | 9/1995 |
| WO | WO 03/042631 | 5/2003 |
| WO | WO 03/104777 | 12/2003 |

* cited by examiner

METHOD AND APPARATUS FOR DETERMINING THE AMOUNT OF SCATTERED LIGHT IN A MACHINE VISION SYSTEM

CROSS-REFERENCE TO RELATED APPLICATIONS

This application is a National Stage application under 35 U.S.C. §371 and claims benefit of International Application No. PCT/SE2008/050473 having an International Filing Date of Apr. 25, 2008, which claims the benefit of priority of EP 07107045.2 having a filing date of Apr. 26, 2007, the contents of both of which are incorporated herein by reference.

TECHNICAL FIELD

The present invention relates to a method and an apparatus in a machine vision system and, in particular to an apparatus allowing for determining the amount of scattered light as well as a method for such determination. The invention further relates to a computer-readable medium for determining the amount of scattered light.

BACKGROUND OF THE INVENTION

Vision systems are widely used for e.g. detecting defects of objects or measuring presence and position of an object placed on a carrier. Such systems comprise a camera or imaging sensor and a light source arranged to illuminate an object to be measured with incident light. Reflected light from the object is detected by the camera and, thus, an image of the object is created. There is often a requirement for imaging multiple characteristics of the same object, such as various three-dimensional (3D) and two-dimensional (2D) characteristics. In the 3D image geometrical characteristics such as width, height, volume etc. of the object are imaged. In the 2D image characteristics such as cracks, structural orientation, position and identity are imaged, for example, through marks, bar code or matrix code. Intensity information in the 2D image is usually imaged in grey scale, but imaging the 2D image in colour, that is to say registering R (red), G (green) and B (blue) components, for example, by means of wavelength-selective filters or light source wavelengths is also common.

Three-dimensional imaging or range imaging is used to obtain a set of range values and the pixel values of a range image represent the distance between the camera "or a fix point" and the measured object. There are a number of well-known techniques for measuring range data. These include laser triangulation, structured light imaging, time-of-flight measurements and stereo imaging.

Further, it is possible to measure scattering of the incident light in the surface layer of the object. That is to say, the light penetrating the material of the object and after scattering is registered when it emerges from the material at a different location from that at which it entered. How this occurs depends on the internal characteristics of the material. When the object and the artefact consist of different types of materials or different internal structures, the incident light scatters differently within the material and, thus, defects of the object is identified by measuring the scattered light. It is to be noted that the term scatter in this context is not to be confused with light diffusively reflected from the surface.

One prior art approach is shown in EP 765 471, which discloses an arrangement and a method for the detection of defects in timber. Here a light source is used in the optical axis, i.e. in the same axis as the sensor when measuring, and separate sensor rows, covering separate virtual lines on the object, for directly reflected light and scattered light are sampled. This method gives very good results if correctly tuned but is difficult to setup and tune.

Another prior art approach is shown in EP 1 432 961, which discloses a method and an arrangement enabling an efficient measurement of objects using triangulation wherein data is outputted and processed from a window around the maximum intensity peak. The disclosed method and arrangement requires that all data around the peak is kept so that it may be used to determine the intensity of the scattered light at a fixed position related to the found peak maximum. Typically the raw window data may be extracted within the sensor, but must be exported to an outside source for further processing, which lowers performance and adds complexity.

These previously known methods to measure scattered light are illustrated in FIG. 4a, which shows an image of an object captured on a two-dimensional sensor. The sensor detects both the light scattered in the regions S1 and S2 in the object and the reflected light R on the object. On both sides of the reflected light R an area of scattered light appears which can be seen in FIG. 4a as S. The intensities (signal strengths) of the reflected light R and the scattered light S1 and S2 in the captured image in FIG. 4a are shown in FIG. 4b.

If the complete image is retrieved from the sensor, the processing to find the intensity of the scattered and reflected light is made by an external signal-processing unit. The output of raw sensor information limits, however, the possible sampling speed. If the sensor has random access capability it is possible to extract only the interesting regions from the sensor, thus retrieving a smaller amount of data from the sensor and a possibility to reach a greater sampling speed. With some sensors it is also possible to have different exposure time and/or read-out amplification for the two regions and also to sum the scattered light from a number of rows to further increase the signal strength.

The scattered light may be collected on one side, S1 or S2, of the reflected light or summed up from both sides, S1 and S2, to further increase the signal strength. If a point light source is used, a multitude of positions around the point may be used together or independent of each other to determine the amount of scattered light.

Efficient measurement of the amount of scattered light is difficult in a triangulation system, since it is necessary to measure the intensity of detected light at a fixed position away from the incoming light as can be seen in FIG. 4b.

SUMMARY OF THE INVENTION

Accordingly, it is an objective with the present invention to provide an improved method of determining the amount of light scattered in an object in a machine vision system comprising: a light source illuminating said object with incident light having a limited extension in at least one direction; and, an imaging sensor detecting light emanating from said object, wherein said emanated light is reflected light on the surface of said object and light scattered in said object, said detected light is resulting in at least one of intensity distribution curve on said imaging sensor having a peak where said reflected light is detected on said imaging sensor.

According to a first aspect of the present invention this objective is achieved through a method as defined in the characterising portion of claim 1, which specifies that in order to determine the amount of light scatter in the object, the method comprises the step of measuring a width of said at least one intensity distribution curve, whereby said measured width indicates the amount of light scattered in said object.

Another objective with the present invention is to provide an improved apparatus for determining the amount of light scattered in an object in a machine vision system comprising: a light source illuminating said object with incident light having a limited extension in at least one direction; and, an imaging sensor detecting light emanating from said object, wherein said emanated light is reflected light on the surface of said object and light scattered in said object, said detected light is resulting in at least one intensity distribution curve on said imaging sensor having a peak where said reflected light is detected on said imaging sensor.

According to a second aspect of the present invention this objective is achieved through an apparatus as defined in the characterising portion of claim 6, which specifies that in order to determine the amount of light scatter in the object, the apparatus comprises means for measuring a width of said at least one intensity distribution curve, whereby said measured width indicates the amount of light scattered in said object.

A further objective with the present invention is to provide an improved computer-readable medium containing computer program for determining the amount of light scattered in an object in a machine vision system comprising: a light source illuminating said object with incident light having a limited extension in at least one direction; and, an imaging sensor detecting light emanating from said object, wherein said emanated light is reflected light on the surface of said object and light scattered in said object, said detected light is resulting in at least one intensity distribution curve on said imaging sensor having a peak where said reflected light is detected on said imaging sensor.

According to a third aspect of the present invention this further objective is achieved through a computer-readable medium as defined in the characterising portion of claim 11, which specifies that in order to determine the amount of light scatter in the object, the computer program performs the step of measuring a width of said at least one intensity distribution curve, whereby said measured width indicates the amount of light scattered in said object.

Further embodiments are listed in the dependent claims.

Thanks to the provision of a method and an apparatus, which uses an incremental function to measure a shape descriptor value of the peak of the intensity distribution curves, it is not necessary to store information about the intensity in the region around the peak and, thus, bandwidth is saved. Also, by measuring scattered light in this way a measure independent of the intensity of the reflected light is achieved which avoids cross-talk between the directly reflected light and the scattered light and which is simpler than prior art approaches to setup and tune to reduce such cross-talk.

Furthermore, in the prior art, combining triangulation and scatter measurements, it is necessary to first determine the position of the peak before being able to measure scattered light at a pre-determined distance from this position (as can be seen in FIG. 4*b*). Thanks to the provision of the inventive method and apparatus it is no longer needed to first determine the position of the peak.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views.

DETAILED DESCRIPTION OF PREFERRED EMBODIMENTS

Figure 1:
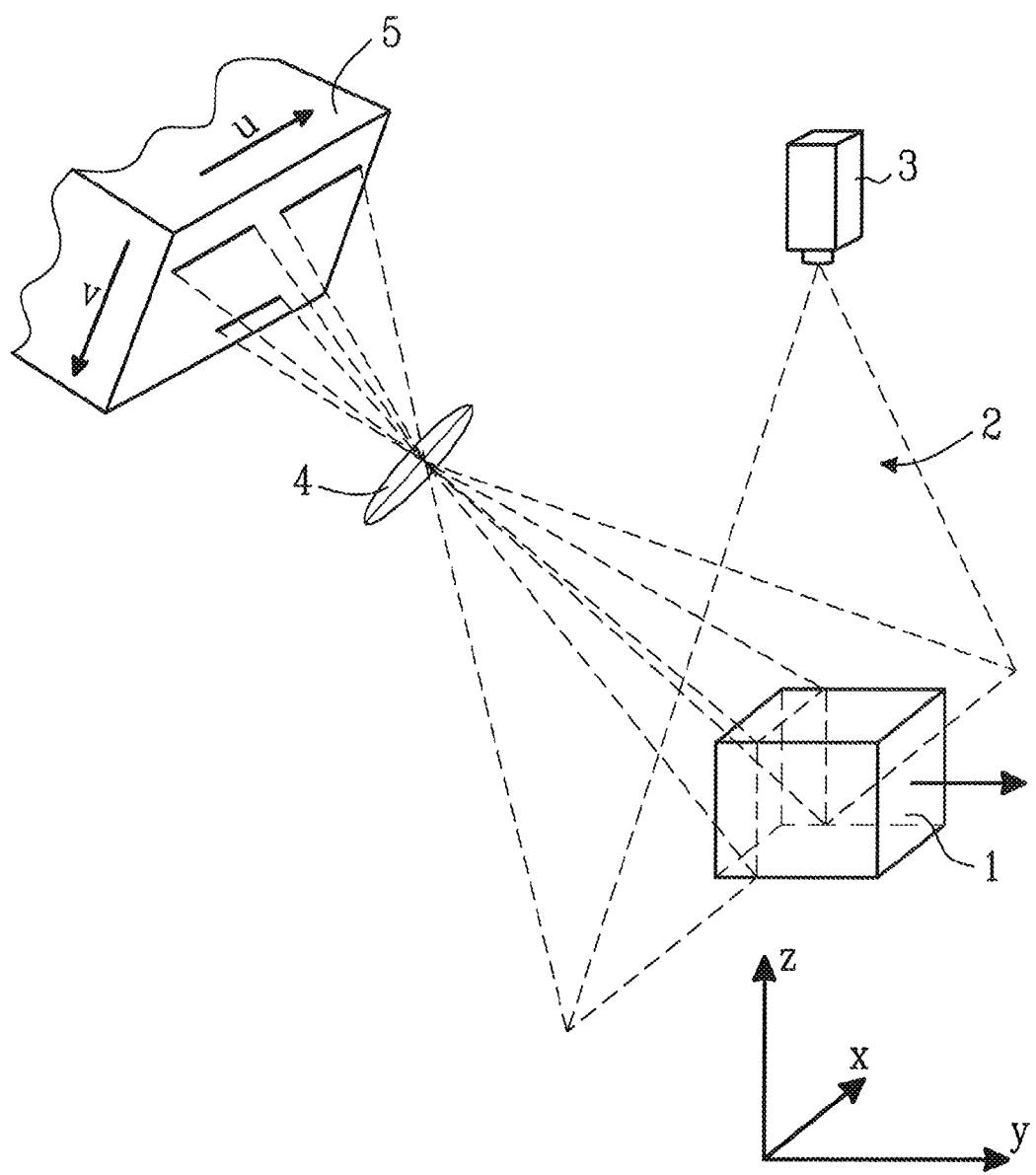
FIG. 1 illustrates schematically an imaging apparatus for measuring the characteristics of an object.

FIG. 1 illustrates schematically an imaging apparatus for measuring the characteristics of an object and for determining the amount of light scattered in an object in a machine vision system. The apparatus comprises at least one light source 3 arranged to illuminate the object 1 with incident light 2 having a limited extension in at least one direction. The at least one light source 3 generates a line of light across the object 1. An imaging sensor 5 is arranged to detect light emanating from the object 1 via a lens 4, wherein the emanated light is reflected light on the surface of the object 1 and light scattered in the object 1 (which is more explained in conjunction with FIG. 2), and to convert the detected light into electrical signals. The detected light is resulting in a multitude of intensity distribution curves on the imaging sensor 5 each having a peak where said reflected light is detected on the imaging sensor 5. The apparatus further comprises means for creating a digital representation of the illuminated cross-section of the object according to the electrical signals. Still further the apparatus comprises means for processing and analyzing the digital representation.

The object and the imaging apparatus are moved in relation to one another in a predefined direction of movement, in the y-direction shown in FIG. 1. In the preferred embodiment of the present invention the object 1 moves relative to the imaging apparatus. The object 1 may e.g. be placed on a conveyor belt which moves or alternatively there is no belt and the object 1 itself moves. Instead of the object 1 moving relative to the imaging apparatus, the relationship may naturally be reversed, that is to say the object 1 is stationary and the imaging apparatus moves over the object when measuring. In still another embodiment both the object 1 and the measuring apparatus move in relation to each other. In a still further embodiment of the present invention, the light source 3, such as a laser, is scanning the object 1.

The light source 3 generates structured light, for example, point light, linear light or light composed of multiple, substantially point or linear segments and may be of any type suitable for the application, for example a laser, a light-emitting diode (LED), ordinary light (light bulb) etc, which are familiar to the person skilled in the art and will not be described further herein. Laser light is preferably used in the preferred embodiment of the present invention.

The light source 3 comprises in one embodiment of the present invention a polarizer (not shown), which polarises the incident light 2. This facilitates in making a distinction between reflected and scattered light, since the reflected light also will be polarized but the scattered light will be polarised to a lesser degree. When the light source 3 comprises a polarizer, it is advantageous to use a sensor that enhances/diminishes light polarized in different directions leading to a reduction of the intensity of the reflected light and, thus, obtaining a better contrast of the scattered light.

The sensor 5 is placed on a predetermined distance from the light source 3. In the preferred embodiment the sensor 5 is an array sensor with u×v pixels (where v is rows and u is columns) but a person skilled in the art will appreciate that the invention may be applied to other types of sensors, such as CCD sensors or CMOS sensors or any other sensor suitable for imaging characteristics of an object. The sensor 5 is in the present system capable of measuring both two-dimensional (2D, intensity) and three-dimensional (3D, range data) information, i.e. is capable of measuring both intensity distribution and geometric profile of the object. The range data is in the preferred embodiment obtained by using triangulation, i.e. the position of the reflected light on the sensor 5 indicates the distance from the sensor 5 to the object 1 when the light source 3 is placed on a predetermined distance from the sensor 5.

The sensor 5 is arranged to detect range information of the object 1 in a plurality of cross-sections of the object illuminated by the light source 3, i.e. it is arranged to repeatedly measure (scan) the object 1, in order to obtain a plurality of cross-section images which are put together into a range image of the object.

Figure 2:
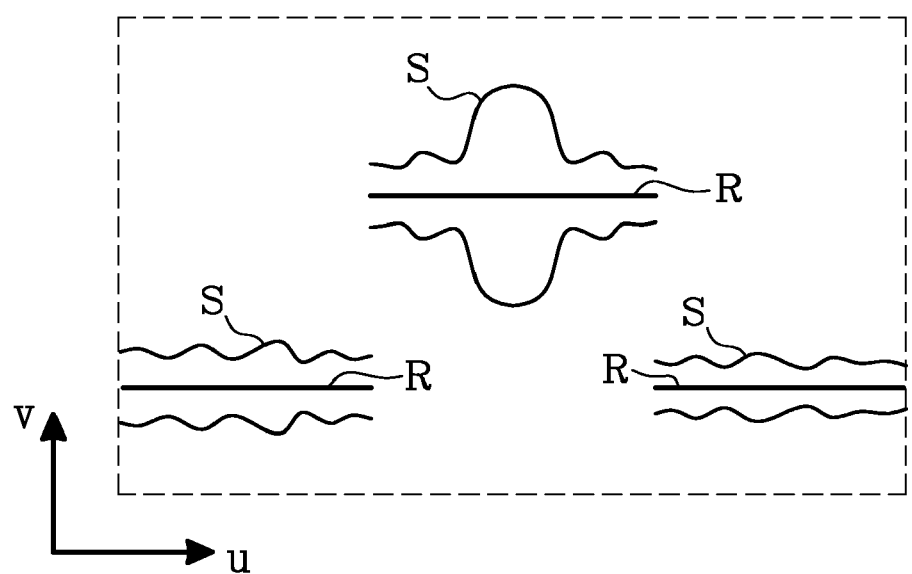
FIG. 2 shows an image of the object in FIG. 1 captured on a two-dimensional sensor.

The reflected R and scattered S light in each cross-section of the object 1 result in an image of the object 1 on the sensor 5 which is illustrated in FIG. 2. As can be seen in FIG. 2, the amount of scattered light varies along the x-direction of the object due to different internal characteristics of the material but possibly also due to defects in the object 1. This is more explained below in conjunction with FIG. 3.

Figure 3:
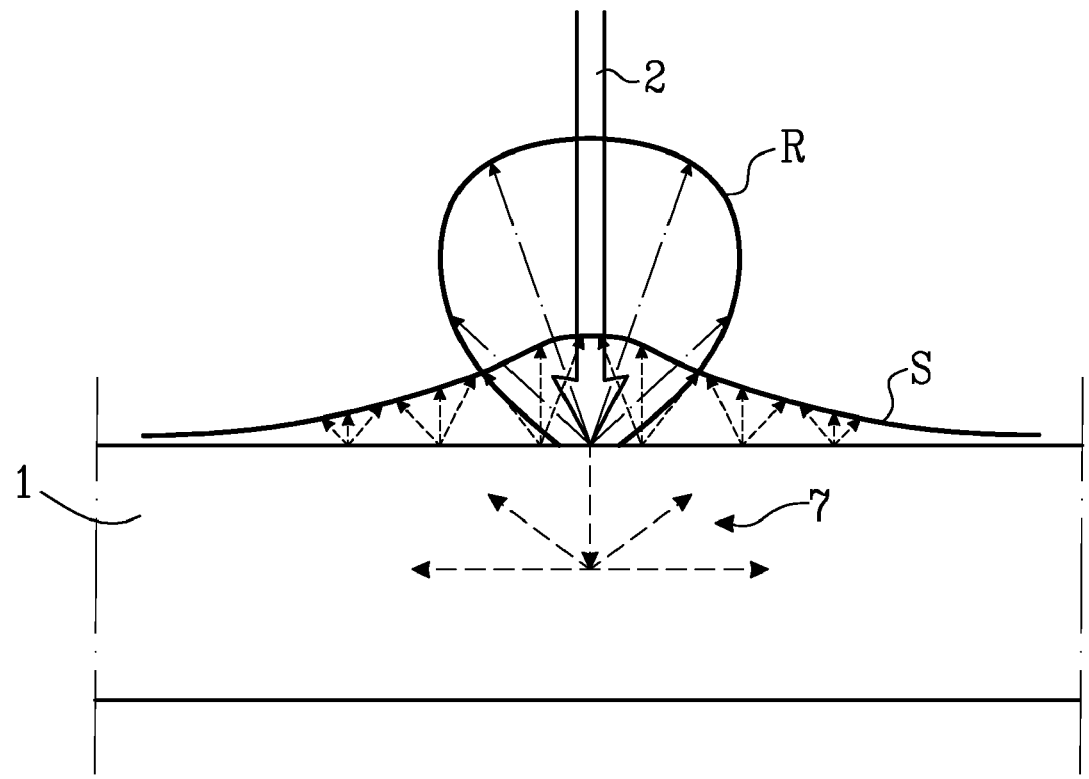
FIG. 3 illustrates how light is reflected upon and scattered within the object.

FIG. 3 shows how light is reflected upon and scattered within the object in one cross-section of the object 1 seen from an x-direction. Thus, the incident light 2 is arranged to hit the surface of the object 1, whereby some of the incident is reflected with both diffuse and specular reflection on the surface with a fanshaped spreading denoted with R in FIG. 3. Some of the incident light 2 penetrates the object 1 and is scattered within the material of the object under the surface (in the surface layer) illustrated with arrows 7 in FIG. 3, whereby it emerges from the material at different locations from that at which it entered. The spreading of the scattered light is denoted S in FIG. 3 and depends on the different internal characteristics of the material.

Figure 4A:
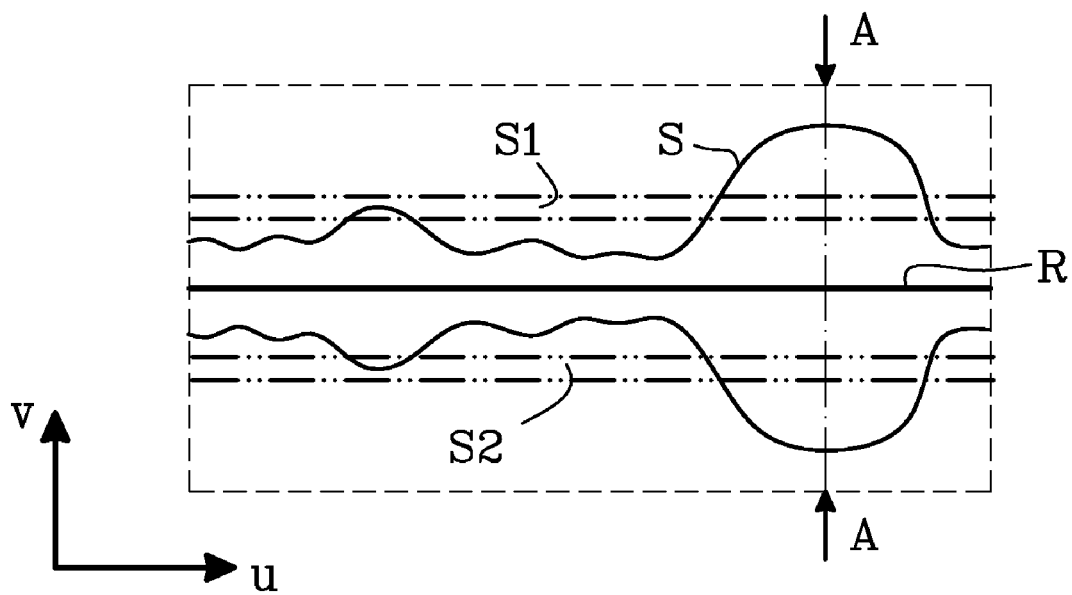
FIG. 4*a* illustrate a prior art method of measuring scattered light from an image of an object captured on a two-dimensional sensor.

In the prior art method of measuring scattered light, light may be collected from regions 51 and/or S2 of the object, shown in FIG. 4a and described above. The regions 51 and S2 must be chosen to be at a distance away from where the incident light hits the object to reduce cross-talk.

Figure 4B:
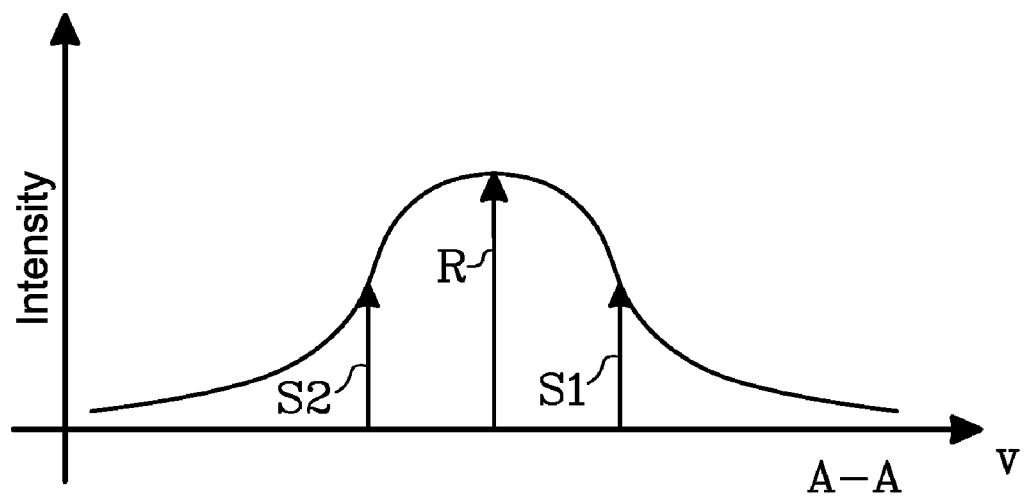
FIG. 4*b* shows an intensity distribution curve in a cross section A-A of the image in FIG. 4*a*.

The inventive imaging apparatus, however, comprises means for measuring a width of said at least one intensity distribution curve, whereby said measured width indicates the amount of light scattered in said object 1. Thus, a function which can measure a shape descriptor value of a peak of an intensity distribution curve instead of measuring the strength/intensity of the signal at a distance away from the entrance of the incident light (as shown in FIGS. 4a and 4b) is used. This measurement may e.g. be the standard deviation, which is a measurement of the width of the peak (assuming a normal (Gaussian) distribution function) as expressed in equation (1). Even if the data does not follow the assumed Gaussian distribution in equation (1) it gives a relevant peak width measurement. The method may be implemented in a way which makes it unnecessary to store information about the intensity in the region around the peak, i.e. it is an incremental measuring method wherein the calculation is done row by row and the originally obtained data may be discarded.

$$\sigma = \sqrt{\frac{1}{\sum f(x)} \times \sum f(x)(x - \bar{x})^2} \tag{1}$$

Figure 5A:
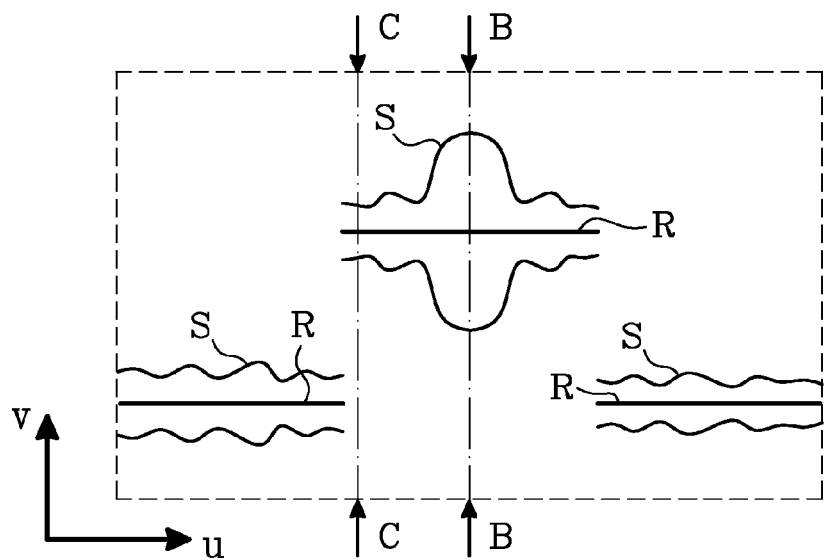
FIG. 5*a* illustrates an image of the object in FIG. 1 captured on a two-dimensional sensor.

Thus, FIG. 5a illustrates an image of the object 1 (shown in FIG. 1) captured on the sensor where the reflected R and scattered S light is seen.

Figure 5B:
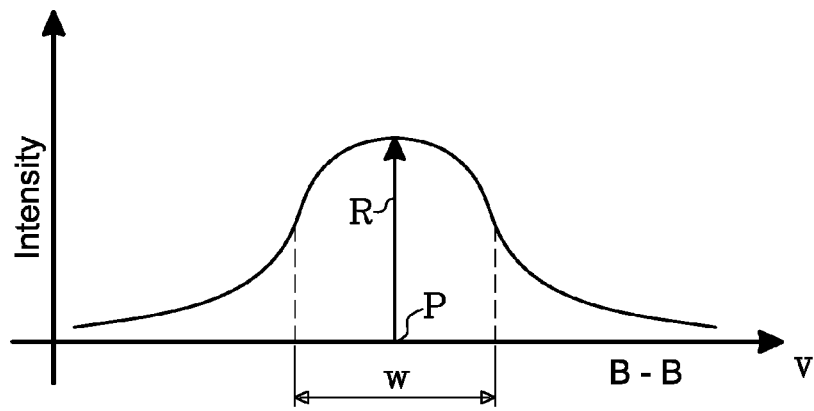
FIG. 5*b* shows an intensity distribution curve in a cross section B-B of the image in FIG. 5*a*.

FIG. 5b illustrates how the intensity of the emanating light is distributed in the form of an intensity distribution curve in the cross-section B-B of FIG. 5a. The intensity distribution curve is a result (combination) of the two curves shown in FIG. 3, i.e. the reflected light R and the scattered light S. The peak position P of the curve is where the maximum reflected light R is captured on the sensor.

According to the preferred embodiment of the invention the scattered light is determined by measuring the width of the intensity distribution curve around the peak position P and is denoted w in FIG. 5b. When the standard deviation is used to determine the width of the curve, w equals two sigma ($2\sigma$), i.e. +/− one sigma.

Figure 5C:
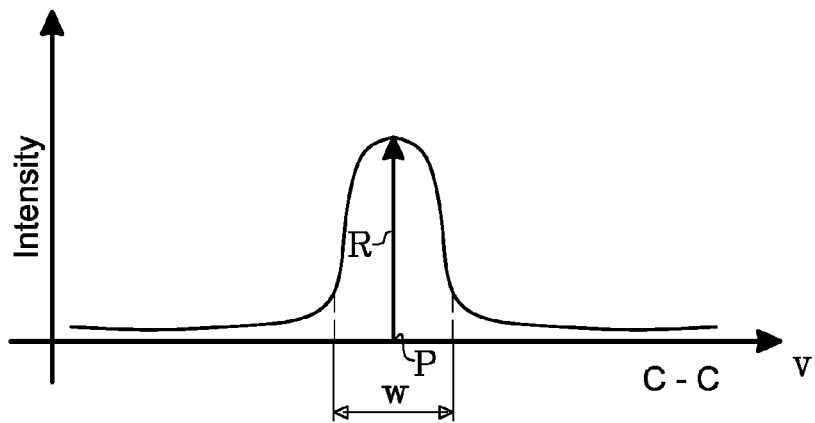
FIG. 5*c* shows an intensity distribution curve in a cross section C-C of the image in FIG. 5*a*.

FIG. 5c illustrates how the intensity of the emanating light is distributed in the cross-section C-C of FIG. 5a. As can be seen from the figure, there is less scattered light in this cross-section than in cross-section B-B. Thus, the measured width, w, of the curve is smaller than in FIG. 5b.

To facilitate the measuring of the width, the peak position P may be calculated. If the peak position is calculated using moments (center of gravity) the zero and first order moments, m0 and m1 are calculated according to equ. (2)-(4). If, additionally, the second order moment, m2 is calculated with equ. (5), there is enough information to recreate the standard deviation using the formula according to equ. (6):

$$m_i = \sum_{x=0}^{N-1} x^i f(x) \tag{2}$$

$$m_0 = \sum f(x) \tag{3}$$

$$m_1 = \sum x f(x) \tag{4}$$

$$m_2 \sum x^2 f(x) \tag{5}$$

$$\sigma = \sqrt{\frac{1}{m_0} \times \left(m_2 - m_1\left(\frac{m_1}{m_0}\right)\right)} \tag{6}$$

Note that the division of m1/m0 is calculated to get the Cog-position and need not be recalculated. There is no need to take the square-root to get the true standard deviation in most cases, since the result only is compared to a threshold value. The standard deviation measurement is also independent of the intensity of the laser peak, which takes away the requirement to measure the reflected light intensity to use for normalization. According to the definition of standard deviation for a normal Gaussian distribution, the standard deviation measures the width where roughly 68% of the values of the distribution are included. That is, for a normal distribution the sum of the values within +/− one sigma width of the average value is around 68% of the total sum of the values of the distribution. The person skilled in the art realizes that the invention is not limited to measuring +/− one sigma of the average value, but also e.g. +/− two sigma may be used leading to around 95% of the total sum.

The calculation of moments in equations (3)-(5) may be implemented very efficiently iteratively using only additions. Furthermore, a measure (standard deviation) which needs no further tuning of distance from peak to sample the scatter intensity is obtained.

According to another preferred embodiment of the present invention, the width of the curve is measured on a pre-defined level of said at least one intensity distribution curve, where a ratio between the intensity on said pre-defined level and a maximum intensity of said at least one curve is 10%-80% and, preferably between 30%-50%.

Thus, according to the preferred embodiment of the present invention a method of determining the amount of light scattered in an object in a machine vision system is provided which comprises: a light source illuminating said object with incident light having a limited extension in at least one direction; and, an imaging sensor detecting light emanating from said object, wherein said emanated light is reflected light on the surface of said object and light scattered in said object, said detected light is resulting in at least one intensity distribution curve on said imaging sensor having a peak where said reflected light is detected on said imaging sensor. The method comprises the step of measuring a width of said at least one intensity distribution curve, whereby said measured width indicates the amount of light scattered in said object.

Further, the measured width is compared with a threshold value, whereby the amount of scattered light correspond to how much said measured width exceeds said threshold value.

In addition to determining the amount of scattered light, range data may be measured by using the position of the peak of the intensity distribution curve in order to obtain the geometrical shape of the object.

To facilitate understanding, many aspects of the invention are described in terms of sequences of actions to be performed by, for example, elements of a programmable computer system. It will be recognized that the various actions could be performed by specialized circuits (e.g. discrete logic gates interconnected to perform a specialized function or application-specific integrated circuits), by program instructions executed by one or more processors, or a combination of both.

Moreover, the invention can additionally be considered to be embodied entirely within any form of computer-readable storage medium, having stored therein an appropriate set of instructions for use by or in connection with an instruction-execution system, apparatus or device, such as computer-based system, processor-containing system, or other system that can fetch instructions from a medium and execute the instructions. As used here, a "computer-readable medium" can be any means that can contain, store, communicate, propagate, or transport the program for use by or in connection with the instruction-execution system, apparatus or device. The computer-readable medium can be, for example but not limited to, an electronic, magnetic, optical, electromagnetic, infrared, or semiconductor system, apparatus, device or propagation medium. More specific examples (a non-exhaustive list) of the computer-readable medium include an electrical connection having one or more wires, a portable computer diskette, a random access memory (RAM), a read only memory (ROM), an erasable programmable read only memory (EPROM or Flash memory), an optical fibre, and a portable compact disc read only memory (CD-ROM).

Thus, a computer-readable medium containing computer program according to a preferred embodiment of the present invention for determining the amount of light scattered in an object in a machine vision system is provided comprising: a light source illuminating said object with incident light having a limited extension in at least one direction; and, an imaging sensor detecting light emanating from said object, wherein said emanated light is reflected light on the surface of said object and light scattered in said object, said detected light is resulting in at least one intensity distribution curve on said imaging sensor having a peak where said reflected light is detected on said imaging sensor, wherein the computer program performs the step of measuring a width of said at least one intensity distribution curve, whereby said measured width indicates the amount of light scattered in said object.

Modifications to embodiments of the invention described in the foregoing are possible without departing from the scope of the invention as defined by the accompanying claims.

Expressions such as "including", "comprising", "incorporating", "consisting of", "have", is used to describe and claim the present invention are intended to be construed in a non-exclusive manner, namely allowing for items, components or elements not explicitly described also to be present. Reference to the singular is also to be construed to relate to the plural and vice versa.

Numerals included within parentheses in the accompanying claims are intended to assist understanding of the claims and should not be construed in any way to limit subject matter claimed by these claims.

The invention claimed is:

1. A method of determining an amount of light scattered in an object in a machine vision system, the method comprising:
   illuminating said object, using a light source, with incident light having a limited extension in at least one direction;
   detecting light emanating from said object, using an imaging sensor, wherein said emanated light is reflected light on the surface of said object and light scattered in said object, said detected light resulting in at least one intensity distribution curve on said imaging sensor having a peak where said reflected light is detected on said imaging sensor; and
   measuring a width of said at least one intensity distribution curve by determining a standard deviation of said intensity distribution curve using said machine vision system, whereby said measured width indicates the amount of light scattered in said object.

2. A method according to claim 1, wherein the method further comprises:
   comparing said measured width with a threshold value, whereby the amount of scattered light corresponds to how much said measured width exceeds said threshold value.

3. A method according to claim 2, wherein the method further comprises:
   measuring range data by using positions of said peaks of said intensity distribution curves in order to obtain the geometrical shape of said object.

4. A method according to claim 1, wherein said width is measured on a pre-defined level of said at least one intensity distribution curve, where a ratio between the intensity on said pre-defined level and a maximum intensity of said at least one curve is 10%-80%.

5. A method according to claim 4, wherein the ratio is between 30%-50%.

6. A method according to claim 4, wherein the method further comprises:
measuring range data by using positions of said peaks of said intensity distribution curves in order to obtain the geometrical shape of said object.

7. A method according to claim 1, wherein the method further comprises:
measuring range data by using positions of said peaks of said intensity distribution curves in order to obtain the geometrical shape of said object.

8. A method according to claim 1, wherein said light source generates one of the following lights: linear light; point light; or, light composed of multiple substantially point or linear segments.

9. An apparatus for determining an amount of light scattered in an object in a machine vision system, the apparatus comprising:
a light source illuminating said object with incident light having a limited extension in at least one direction;
an imaging sensor detecting light emanating from said object, wherein said emanated light is reflected light on the surface of said object and light scattered in said object, said detected light resulting in a multitude of intensity distribution curves on said imaging sensor having a peak at a position where said reflected light is detected on said imaging sensor; and
measuring means for measuring a width of said at least one intensity distribution curve by determining a standard deviation of said intensity distribution curve, whereby said measured width indicates the amount of light scattered in said object.

10. An apparatus according to claim 9, wherein the apparatus further comprises means for comparing said measured width with a threshold value, whereby the amount of scattered light corresponds to how much said measured width exceeds said threshold value.

11. An apparatus according to claim 10, wherein the apparatus further comprises means for measuring range data by using the position of said peak of said intensity distribution curve in order to obtain the geometrical shape of said object.

12. An apparatus according to claim 9, wherein the means for measuring said width is arranged to measure said width on a pre-defined level of said at least one intensity distribution curve, where a ratio between the intensity on said pre-defined level and a maximum intensity of said at least one curve is 10%-80%

13. An apparatus according to claim 12, wherein the ratio is between 30%-50%.

14. An apparatus according to claim 12, wherein the apparatus further comprises means for measuring range data by using the position of said peak of said intensity distribution curve in order to obtain the geometrical shape of said object.

15. An apparatus according to claim 9, wherein the apparatus further comprises means for measuring range data by using the position of said peak of said intensity distribution curve in order to obtain the geometrical shape of said object.

16. An apparatus according to claim 9, wherein said light source is arranged to generate one of the following lights: linear light; point light; or, light composed of multiple substantially point or linear segments.

17. A computer-readable medium containing computer program for determining an amount of light scattered in an object in a machine vision system, which computer program when executed causes a method to be performed comprising:
illuminating said object, using a light source, with incident light having a limited extension in at least one direction;
detecting light emanating from said object, using an imaging sensor, wherein said emanated light is reflected light on the surface of said object and light scattered in said object, said detected light resulting in a multitude of intensity distribution curves on said imaging sensor having a peak at a position where said reflected light is detected on said imaging sensor; and
measuring a width of said at least one intensity distribution curve, whereby said measured width indicates the amount of light scattered in said object.

* * * * *

UNITED STATES PATENT AND TRADEMARK OFFICE
CERTIFICATE OF CORRECTION

| | | |
|---|---|---|
| PATENT NO. | : 8,213,025 B2 | Page 1 of 1 |
| APPLICATION NO. | : 12/531421 | |
| DATED | : July 3, 2012 | |
| INVENTOR(S) | : Mattias Johannesson, Henrik Turbell and Per Holm | |

It is certified that error appears in the above-identified patent and that said Letters Patent is hereby corrected as shown below:

Column 10, Line 8 (Claim 12), delete "80%" and insert -- 80%. -- therefor.

Signed and Sealed this
Eleventh Day of September, 2012

David J. Kappos
*Director of the United States Patent and Trademark Office*